United States Patent [19]

Vanlerberghe et al.

[11] 4,087,466
[45] May 2, 1978

[54] POLYCONDENSATION OF GLYCIDOL ON ALPHA DIOLS WITH FATTY CHAIN WITH ALKALINE CATALYSTS, PRODUCTS THUS OBTAINED AND UTILIZATION

[75] Inventors: Guy Vanlerberghe, Montjay-la-Tour; Henri Sebag, Paris, both of France

[73] Assignee: L'Oreal, Paris, France

[21] Appl. No.: 678,030

[22] Filed: Apr. 19, 1976

Related U.S. Application Data

[60] Division of Ser. No. 561,630, Mar. 24, 1975, Pat. No. 3,966,398, which is a division of Ser. No. 384,635, Aug. 1, 1973, Pat. No. 3,928,224, which is a continuation-in-part of Ser. No. 142,409, May 11, 1971, Pat. No. 3,821,372.

[30] Foreign Application Priority Data

May 12, 1970 Luxembourg .......................... 60900

[51] Int. Cl.² .................... C07C 43/10; C07C 41/02
[52] U.S. Cl. ............................................. 260/615 B
[58] Field of Search ..................................... 260/615 B

[56] References Cited

U.S. PATENT DOCUMENTS

| 2,536,685 | 1/1951 | Harman et al. ............. 260/615 B X |
| 3,427,248 | 2/1969 | Lamberti et al. ............ 260/615 B X |
| 3,708,364 | 1/1973 | Kalopissis et al. ........ 260/615 B UX |
| 3,719,636 | 3/1973 | Wojtowicz et al. ............. 260/615 B |

*Primary Examiner*—Howard T. Mars
*Attorney, Agent, or Firm*—Cushman, Darby & Cushman

[57] ABSTRACT

A method of preparing a novel non-ionic surfactant usefully employed in a cosmetic composition having the formula

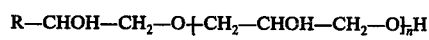

wherein R is selected from the group consisting of aliphatic, cycloaliphatic and arylaliphatic radicals and mixtures thereof having 7–21 carbon atoms, $n$ is greater than 1 and equal to or less than 10, the method comprising condensing on an α-diol having the formula

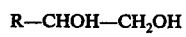

wherein R has the above meaning, $n$ moles of glycidol having the formula

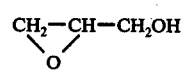

in the presence of an alkaline catalyst at a temperature of 120°–180° C.

4 Claims, No Drawings

POLYCONDENSATION OF GLYCIDOL ON ALPHA DIOLS WITH FATTY CHAIN WITH ALKALINE CATALYSTS, PRODUCTS THUS OBTAINED AND UTILIZATION

This is a division of application Ser. No. 561,630, filed Mar. 24, 1975, now U.S. Pat. No. 3,966,398, which is a division of application Ser. No. 384,635, filed Aug. 1, 1973, now U.S. Pat. No. 3,928,224 which is a continuation-in-part of application Ser. No. 142,409 filed May 11, 1971, now U.S. Pat. No. 3,821,372.

The present invention relates to a process for the preparation of polyhydroxyl non-ionic compounds, by polycondensation of glycidol on alpha diols with fatty chain, in alkaline catalysis, and to the products thus obtained.

This process of the present invention produces non-ionic surfactants having the formula

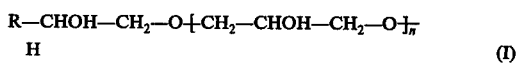
(I)

in which R designates a radical or a mixture of radicals, namely aliphatic, cycloaliphatic and/or arylaliphatic with 7 to 21 carbon atoms, aliphatic chains which can be saturated or unsaturated, linear or branched, and which can present oxygen and/or sulfur atoms, especially 1 to 6, preferably 2 to 4 and more preferably 2 or 3 ether, thioether and/or hydroxymethylene groups, $n$ is any whole or decimal number greater than 1 and equal to or less than 10 and indicates the average degree of polymerization. In the process of this invention, there are condensed on an alpha diol having the formula:

R—CHOH—CH$_2$OH   (II)

where R has the above indicated meaning, in the presence of an alkaline catalyst or a mixture of alkaline catalysts, $n$ molecules glycidol having the formula:

As examples of radicals represented by R, the following are mentioned:

(a)

hexyl, octyl, decyl, dodecyl, tetradecyl, hexadecyl, octadecyl, eicosyl and heneicosyl;

(b)

R'—O—CH$_2$—,

R'—S—CH$_2$—,

R'—S—CH$_2$—CH$_2$—O—CH$_2$—,

R'—S—CH$_2$—CH$_2$—CH$_2$—O—CH$_2$—,

R'—CHOH—CH$_2$—O—CH$_2$— and

R'—CHOH—CH$_2$—S—CH$_2$—, wherein R' designates one of the radicals listed under (a);

(c)

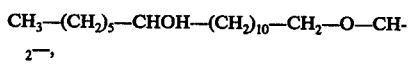

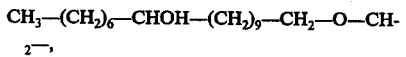

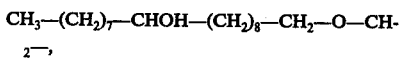

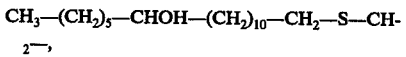

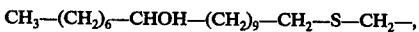

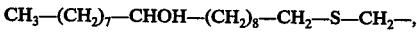

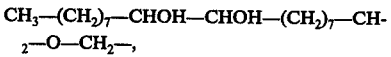

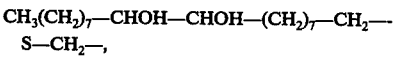

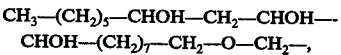

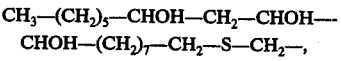

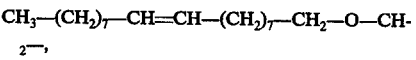

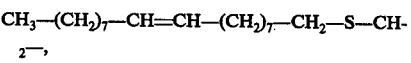

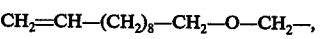

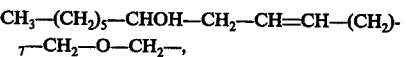

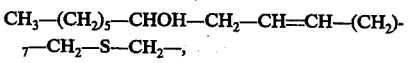

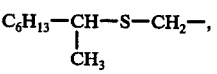

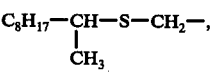

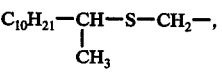

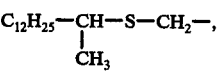

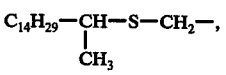

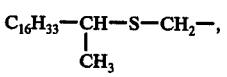

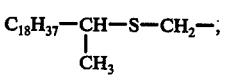

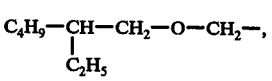

-continued

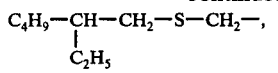
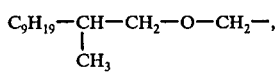
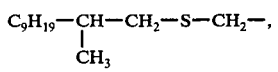
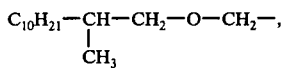
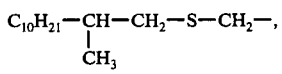
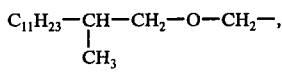
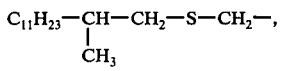
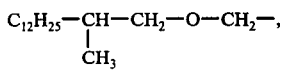
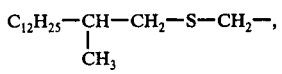
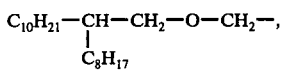
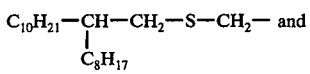 and

R''—O—CH$_2$—, wherein R'' represents 3,7,11,15-tetramethyl hexadecyl;

(d)
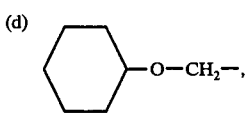

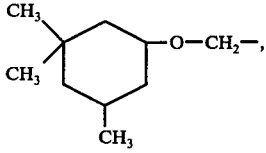

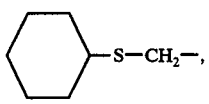

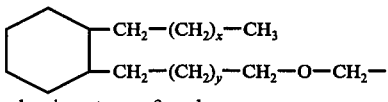
wherein x + y = 8, and

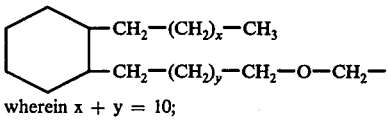
wherein x + y = 10;

-continued (e)
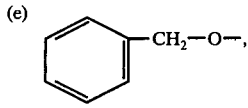

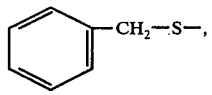

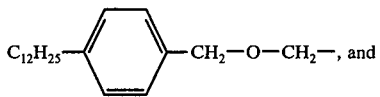

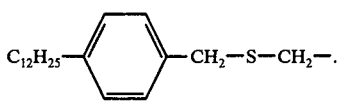

R on the other hand can designate a mixture of the radicals mentioned above.

The condensation of glycidol on alcohols in the presence of alkaline catalysts is known especially in U.S. Pat. Nos. 2,089,569 and 2,131,142 of Ludwig Orthner and Claus Heuck.

However, the process indicated in these patents does not permit production of products that are sufficiently soluble from simple fatty alcohols or those which present an ether or thioether group. In fact, glycidol largely condenses on itself, forming polyglycerols that are immiscible with lipophilic chain compounds. This is not astonishing since glycidol is well known for its pronounced tendency to polymerize at ordinary temperature in the presence of basic catalysts such as methylamine, pyridine, sodium, potassium or sodium methylate, and this tendency to polymerization has been pointed out, particularly in the Journal of Polymer Science pt.A-1, 4(5), 1253-9 (1966) (English). See also Chemical Abstracts vol. 64, 19781.

On the other hand, it is very surprising to observe that by slow addition of glycidol to long chain alpha diols in the presence of alkaline catalysts at a temperature of 120°–180° C, preferably 140° to 160° C, the reaction medium remains perfectly homogeneous and that hydrosolubility is reached for a relatively low mean degree of polymerization $n$.

The alpha diols thus appear to constitute a special group in the class of alcohols, whether it is a matter of simple alcohols or of alcohols comprising an ether and/or a thioether group.

Polycondensation of glycidol is effected preferably in an inert atmosphere, e.g. nitrogen. A mixture of compounds is formed that are all of the general formula (I), but for which compounds the number of fixed glycidol molecules can be greater or less than the statistical mean value corresponding to the number of glycidol molecules used per molecule of mercaptan. As a result there is obtained a mixture of compounds with different values for $n$, in other words, having longer or shorter hydrophilic chains, the whole of the $n$ values being statistically distributed about a mean value corresponding to the number of glycidol molecules per alpha diol molecule.

The alpha diols of formula (II) which are used as starting material can be prepared by conventional processes such as:

hydroxylation of non saturated derivatives; hydrolysis of substituted oxirane cycles; condensation of fatty chain mercaptans on glycidol; condensation of thioglycerol on alkyl halides or on fatty chain alpha olefins; and condensation of glycerol, glycerol isopropylidene and thioglycerol on substituted oxiranes or on alkyl tosylates or mesylates etc.

As basic catalysts there are used alkaline hydroxides or alcoholates, preferably of sodium or potassium, in proportions of 0.5 to 10 mole % and preferably from 4 to 8 mole % with reference to the utilized diols.

The addition of glycidol to the reaction medium is effected slowly. It can last from several minutes to several hours (up to about 4 hours).

In the case of polyhydroxyl thioethers, the corresponding sulfoxides can be prepared according to a known process by addition of hydrogen peroxide, 30–35%, possibly in the presence of 0.5 to 10% by weight of a lower carboxylic acid, e.g. acetic acid, which allows utilization of less glycidol to obtain water solubility.

The invention likewise concerns products obtained according to the above described process. Most are more or less consistent pastes whose properties differ according to the nature of the R radical, of the intermediate ether, thioether or hydroxymethylene group when they are present, and upon the degree of polymerization $n$.

These are surfactants, and as the case may be, they are foaming agents, softeners, thickeners, peptizers or emulsifiers. Their water solubility is attained with a relatively low degree of polymerization $n$.

Thus, for example, products for which the lipophilic part is constituted by 11 to 14 carbon atoms are foaming agents which are remarkable in comparison to conventional non-ionic compounds, for substantially lower $n$ values.

With longer hydrocarbon chains there are obtained thickening or emulsifier products. These emulsifiers are especially effective for polar oils and similar products.

The intrinsic nature of the hydrophilic groups of these non-ionic compounds permits, moreover, a very good compatibility with concentrated alkali solutions, which property permits their use in the textile industry, e.g. for mercerizing.

The present invention also relates to compositions intended to be used in cosmetics, especially shampoos, hair dyes, dispersions, emulsions or solutions, these compositions being characterized substantially in that they contain from 0.1 to 80 percent by weight of at least one product of formula (I).

The present invention also relates to dispersions and emulsions, and especially dispersions or oil-in-water emulsions of polar oils.

As examples of polar oils there can be mentioned vegetable oils such as peanut oil, castor oil, sweet almond oil, olive oil and corn oil, esters of glycerol such as glycerol stearates, glycerides of fatty acids such as triglycerides of octanoic and decanoic acids, fatty alcohols such as 2-octyl 1-dodecanol, fatty acids such as stearic acid, alkyl esters of fatty acids such as alkylesters of adipic, myristic and palmitic acid and alkyl esters of fatty acids of lanolin and especially isopropyl myristate or palmitate, ethyl palmitate, butyl stearate, 2-ethyl hexyl palmitate and isopropyl esters of fatty acids of lanolin and solvents such as chlorobenzene, 1,4-dichloro butane, monochloro butane, trichloroethylene and perchloroethylene.

The "oil-in-water" emulsions can include from 2 to 60% oil, 0.1 to 20% emulsifier and 30 to 80% water.

Polyhydroxyl non-ionic compounds of the present invention can also be used to disperse alkaline earth soaps and especially calcium and magnesium soaps.

For each gram of soap to be dispersed, there is utilized 0.02–1 g, preferably 0.1–0.2 g of the compounds of formula (I) in 100 ml solution to 400 ppm calcium chloride.

The test used to show this property is the one proposed by J. Alba Mendoza and C. Gomez Herrera at the fifth international detergents conference in Barcelona in 1968.

The table below shows, for certain compounds of formula (I) whose preparation appears in the examples which follow, the minimum quantity Q (in milligrams) that is necessary to disperse 50 mg sodium oleate in 50 ml water with hardness corresponding to a content of 400 ppm calcium chloride, under the test conditions described by Alba Mendoza.

The lauryl sulfate of sodium which appears in the table was selected as control because it represents the medium type of dispersant for alkaline earth soaps.

| Compounds of Example | Q mg |
|---|---|
| 1 | $5 < Q < 10$ |
| 2 | $5 < Q < 6$ |
| 4 | $5 < Q < 10$ |
| 8 | $5 < Q < 10$ |
| control: sodium lauryl sulfate | 68 |

The compositions, dispersions and emulsions can be stored in aerosol cans under pressure and containing conventional aerosol propellants such as monochlorotrifluoromethane or dichlorodifluoromethane. They can also include various adjuvants, e.g. other surfactants.

The compatibility of most of the compounds of formula (I) with aqueous solutions of alkaline hydroxides, e.g. with 40% NaOH, is one of their particularly advantageous properties which permits their use in the textile industry, e.g. for mercerizing.

EXAMPLE 1

A mixture of compounds of formula (I) in which R indicates a mixture of alkyl radicals having 9 to 12 carbon atoms, $n$ has a mean statistical value of 3.5, is prepared by polycondensation of the glycidol on a mixture of $C_{11}$–$C_{14}$ alpha diols sold by Archer Daniels Midland Co., under the tradename ADOL 114.

To 54 g of the above mentioned diols in a mixture, with a hydroxyl number of 520, there are added 3.75 ml of a solution of sodium methylate in methanol to a concentration of 4.6 meq/g (milliequivalents/gram). The mixture is heated to 155° C, eliminating the methanol, and there are introduced, drop by drop, in the course of 70 minutes, 72 g of glycidol (0.87 equivalents epoxide).

The product thus obtained is a thick brown oil that is perfectly soluble in water and in 40% sodium hydroxide. The Kraft point for a 1% solution is below 10° C. The cloud point for a 0.5% solution is above 100° C, both in demineralized water and in water that contains 10% NaCl.

The foam heights measured by use of the Ross-Miles apparatus, for concentrations of 0.05%, 0.2% and 0.5% at 35° C in hard water (corresponding to 340 ppm CaCO$_3$) are respectively 13 cm, 18.5 cm and 20 cm.

When applied as a 5% aqueous solution to the eyes of rabbits, the product is absolutely non-irritating.

EXAMPLE 2

A mixture of compounds of formula (I) in which R is a mixture of alkyl radicals having 13 to 16 carbon atoms, $n$ has a mean statistical value of 3.1, is prepared by polycondensation of the glycidol on a mixture of $C_{15}$–$C_{18}$ alpha diols sold by the Archer Daniels Midland Co. under the name ADOL 158.

To 43 g of the mixture of the mentioned diols with a hydroxyl number of 430, there is added 1 ml of solution of sodium methylate in methanol, to the concentration of 4.6 meq/g and, at 155° C, drop by drop, in the course of 105 minutes, 38 g of glycidol.

The product thus obtained is water soluble and has a very slight opalescence.

The Kraft point is below 0° C.

The cloud point for a 0.5% solution is above 100° C in demineralized water as well as in water that contains 10% NaCl.

EXAMPLE 3

A mixture of compounds of general formula (I) in which R is the radical R′—S—CH$_2$—, wherein R′ represents a mixture of straight chain and branched $C_{12}$–$C_{15}$ alkyl radicals of which about 14% are 2-methyl alkanols sold by the Shell Co. under the name Dobanol 25, $n$ representing a mean statistical value of 2.5, is prepared as follows.

In a first stage, glycerol alkyl thioethers are prepared by reaction of the above mentioned alcohols with methane sulfochloride, with subsequent condensation of the thioglycerol in an alkaline medium.

205 g (1 mole) of Dobanol 25 are mixed with 101 g triethylamine in 250 ml benzene and in the course of 90 minutes there are introduced, at 30°–40° C, 114 g (1 mole) methane sulfochloride. After 1 hour of additional stirring the level of reaction is 97.5%.

After filtration of the triethylamine hydrochloride, there is added a stoichiometric quantity of the sodium derivative of the thioglycerol under nitrogen. The reaction mixture is brought to 100° C with partial elimination of the benzene and with addition of 30 ml of methanol in the course of the reaction to avoid thickening of the reaction mass.

The alkyl thioglycerol is then expanded with 100 ml water, decanted and then vacuum dried to a temperature of 100° C.

To 65 g (0.2 mole) of the product thus obtained, there are added 2 ml of methanol solution of sodium methylate to 4.6 meq/g. The mixture is heated to 155° C and there is then added, dropwise in the course of 90 minutes, 0.5 mole glycidol.

The thioether prepared in this way can be oxidized to sulfoxide with stoichiometric quantities of hydrogen peroxide in the presence of 0.5% acetic acid, yielding a product that is water soluble.

The Kraft point at 1% is 19° C. The cloud point of the product at 0.5% is 80° C in demineralized water and 68° C in water that contains 10% NaCl.

The foam heights measured with the Ross-Miles apparatus at 35° C in hard water are respectively 10.5 cm, 16.5 cm and 18 cm for concentrations of 0.05%, 0.2% and 0.5%, respectively.

EXAMPLE 4

A mixture of compounds substantially identical with those of Example 3, with the difference that $n$ represents a mean statistical value of 3 is also prepared. This slight increase in the value of $n$ results in an increase in the range of solubility of the polyhydroxyl sulfoxide, i.e. a lowering of the Kraft point to 8° C and an elevation of the cloud point above 100° C in demineralized water, and to 85° C in water that contains 10% NaCl.

The foam heights are not much changed, however. They are respectively 10.5 cm, 15.5 cm and 18.5 cm.

EXAMPLE 5

Preparation of a mixture of compounds of the general formula (I) in which R is a radical R′—S—CH$_2$—, R′ being an oleyl group (the hydrocarbon derivative radical of oleic acid) and $n$ is a mean statistical value of 6.

In a first stage there is prepared oleyl thioglycerol by the addition of 78 g oleyl alcohol (0.3 mole) to 30 g triethylamine in 40 ml benzene. There are then added, at ambient temperature in the course of 75 minutes, 34 g methane sulfochloride.

After a night at 25° C the reaction is total. The triethylamine hydrochloride that has formed is filtered off and the sodium derivative of the thioglycerol is added. The benzene is partly eliminated and 50 ml methanol are added. After 2½ to 3 hours of stirring at 40°–45° C the level of reaction is 95%.

The thioether that is obtained is salted out with 50 ml water at 70° C and dehydrated at 95° C.

The theoretical amount of glycidol is added at 155° C in the presence of 3 ml of a methanol solution of sodium methylate to have a statistical mean of 6 —CH$_2$—CHOH—CH$_2$—O— units per fatty chain. A brown water soluble paste with slight opalescence, perfectly soluble in 40% NaOH, is obtained.

The Kraft point is less than 0° C. The cloud point is above 100° C in demineralized water.

EXAMPLE 6

Preparation of a mixture of compounds of the general formula (I) in which R is the radical $C_{16}H_{33}$—O—CH$_2$— and $n$ is the mean statistical value of 4.

This mixture of compounds is prepared by polycondensation of glycidol in the same conditions as in the earlier examples, on the cetyl ether of glycerol having the formula

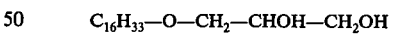

$C_{16}H_{33}$—O—CH$_2$—CHOH—CH$_2$OH prepared as follows:

To 976 g (4 moles) cetyl alcohol there are added 3.5 ml of an acetic solution of boron fluoride and then drop by drop in the course of 2 hours, 407 g (4.4 moles) epichlorohydrin at 70°–75° C.

The product thus obtained is then washed three times with 700 ml water at 80° C and then distilled at 178°–185° C under a pressure of 0.5 to 1 mm Hg.

To 327 g (0.98 mole) of the chlorated derivative thus obtained there are added 330 g tertiobutyl alcohol, and then at 50° C, 200 g (2 moles) of 40% NaOH. The reaction mixture is then held at 80° C for 30 minutes. There are then added 200 ml water to salt out the cetyl glycidyl ether that is distilled after elimination of the tertiobutyl alcohol at 150°–155° C/0.1 mm.

To obtain the corresponding alpha diol, there is prepared in an intermediate phase the acetic ester, by heating 210 g (0.7 mole) of cetyl glycidyl ether with 46 g (0.77 mole) glacial acetic acid in the presence of 9 to 10 ml triethylamine for 2 to 4 hours.

The acetic ester is then saponified in an alcohol medium and washed three times with boiling water.

To 32 g (0.1 mole) cetyl monoether of the obtained glycerol there are added 1.5 ml sodium methylate in solution in methanol and then in the course of 3 hours, 30 g (0.4 mole) glycidol at 155° C.

The product thus prepared is a clear chestnut colored odorless wax that is perfectly soluble in water and in 40% NaOH.

The Kraft point for a 1% solution is 42° C. The cloud point for a 0.5% solution is above 100° C, for demineralized water as well as for water that contains 10% NaCl.

EXAMPLE 7

Preparation of a mixture of compounds of the general formula (I) in which R is the radical $C_{12}H_{25}-S-CH_2-CH_2-CH_2-O-CH_2-$ and $n$ has a mean statistical value of 3.

This mixture of compounds is prepared by polycondensation of the glycidol on glycerol dodecyl thiopropyl ether. This latter product is obtained by addition of 30.5 g (0.15 mole) lauryl mercaptan to 20 g (0.15 mole) glycerol allyl ether (prepared by the process indicated by Daniel Swern JACS vol. 71 (1949) page 1154) in the presence of 0.25 g azodiisobutyronitrile at 70° C. Duration of the reaction is 1½ hour.

To 25 g (0.075 mole) glycerol dodecyl thiopropyl ether thus prepared there are added 1 ml of methanol solution of sodium methylate, 5.2 meq/g, and then drop by drop at 150° C in the course of 1 hour, 18 g glycidol (0.22 equivalents epoxide).

The mixture of products that is obtained is water soluble. The Kraft point for a 1% solution is 6° C. The cloud point at 0.5% concentration is above 100° C in demineralized water and 79° C in water containing 10% NaCl.

EXAMPLE 8

Preparation of a mixture of compounds of the general formula (I) in which R is the radical $R'-CHOH-CH_2-S-CH_2-$, with $R'$ being a mixture of alkyl groups, nonyl to dodecyl, and $n$ has a mean statistical value of 3.

The initial alpha diol is prepared by condensation of the thioglycerol on a mixture of fatty chain oxiranes, sold under the name of NEDOX 1114 by the Archer Daniels Midland Company.

To 21.5 g thioglycerol (0.2 mole) there are added 2 g of methanol solution of sodium methylate (0.01 mole) and then, drop by drop, at a temperature of 80°–85° C, 42.8 g (0.2 equivalent) of NEDOX 1114.

The reaction is exothermal during the whole addition, which requires 20 minutes.

A nitrogen atmosphere is used.

Five minutes after the conclusion of the addition, there are no more free —SH groups. The product is heated to 150° C with elimination of the methanol from the sodium methylate solution and there are added, dropwise in the course of 90 minutes, 48 g (0.6 equivalents) glycidol.

The product obtained is a thick oil which is brown in coloration, soluble in water and in 40% NaOH.

The Kraft point is below 0° C. The cloud point is 65° C in demineralized water and 45° C in a 10% NaCl aqueous solution.

The foam heights measured by means of the Ross-Miles apparatus, for concentrations of 0.05%, 0.2% and 0.5% are 4.5 cm, 11 cm and 16 cm respectively.

EXAMPLE 9

Preparation of a mixture of compounds of the general formula (I) in which R is the radical

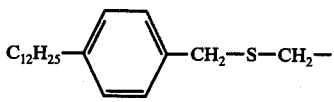

and $n$ has the mean statistical value of 3.5.

The dodecylbenzyl thiopropane diol is prepared by condensation at 60° C of 17.5 g (0.06 mole) dodecyl benzyl mercaptan on 4.8 g (0.06 equivalent) glycidol in the presence of 0.9 ml methanol solution of sodium methylate, 4.6 meq/g.

The diol thus prepared is heated to 155° C, at which temperature there are added drop by drop 16.5 g (0.21 equivalent) glycidol.

The polyhydroxyl thioether is a brown paste that can be dispersed in water.

By oxidation with stoichiometric quantities of hydrogen peroxide in the presence of 0.5% by weight acetic acid, there is obtained a product that is soluble in water, whose Kraft point is 75° C and whose cloud point in demineralized water is above 100° C.

EXAMPLE 10

Preparation of a mixture of compounds of formula (I) in which R is the dodecyl radical and $n$ has the mean statistical value of 3.5 by polycondensation of glycidol on tetradecane diol-1,2

The tetradecane diol-1,2 that is used is prepared by hydroxylation of tetradecene-1,2 sold by Gulf Oil Company, Houston (by the method indicated in Organic Reactions vol. VII, pages 399–400, by Roger Adams).

There are added to 46 g (0.2 mole) tetradecane diol-1,2, 3 ml of solution of sodium methylate in methanol at the concentration of 4.96 meq/g. This mixture is heated to 155° C, the methanol being driven off, and there are introduced at this temperature, drop by drop, in the course of 1 hour and 15 minutes, 52 g glycidol (0.7 mole) under nitrogen.

The product thus obtained has the form, when cold, of a clear chestnut wax which is soluble in water and in 40% soda.

The cloud point is above 100° C both in demineralized water and in water that contains 10% NaCl.

The foam heights measured by means of the Ross-Miles apparatus for concentrations of 0.05%, 0.2%, and 0.5% at 35° C in hard water are respectively 10 cm, 19 cm and 21 cm.

EXAMPLE 11

Preparation of a mixture of compounds of formula (I) in which R is a mixture of decyl and dodecyl radicals and $n$ has the mean statistical value of 3, by polycondensation of glycidol on a 50/50% mixture by weight dodecane diol-1,2 and tetradecane diol-1,2.

The mixture of alpha diols is prepared after hydroxylation of the corresponding alpha olefins by the process indicated in the previous example.

There are added to 400 g of such a mixture, 3.72 equivalents of hydroxyl groups, 28.2 ml solution of sodium methylate in methanol, 4.96 meq/g.

The reaction mixture is heated to 155° C with elimination of the methanol and there are added drop by drop 414 g distilled glycidol (5.58 equivalents) in the course of 3½ hours.

The mixture of the compound thus obtained is soluble in water and in 40% sodium hydroxide.

The Kraft point is less than 0° C and the cloud points are above 100° C in demineralized water and 95° C in water with 10% NaCl.

The foam heights measured by means of the Ross-Miles apparatus are respectively 14 cm, 19 cm and 20 cm for concentrations of 0.05%, 0.2% and 0.5% at 35° C in hard water.

EXAMPLE 12

Preparation of a mixture of compounds of formula (I) in which R is an octyl radical and $n$ has a mean statistical value of 2.5.

This mixture of compounds is obtained by the polycondensation of 40 g of glycidol (0.5 epoxide equivalent) on 35 g (0.2 equivalent) of decane 1,2-diol in the presence of 0.45 g of sodium methylate in methanol (0.008 equivalent) at a temperature of 155° C and under a nitrogen atmosphere.

There is thus obtained a product which is present in the form of a very thick brown oil soluble in water and 40% NaOH, having a cloud point greater than 100° C both in demineralized water and in water containing 10% NaCl.

The foam heights measured by means of the Ross-Miles apparatus for concentrations of 0.05%, 0.2% and 0.5% are, respectively, 9 cm, 20 cm and 18 cm.

EXAMPLE 13

Preparation of a mixture of compounds of formula (I) in which R is a tetradecyl radical and $n$ has the mean statistical value of 1.3.

To 38.5 g of hexadecane 1,2-diol (0.15 mole) there are added 2.8 ml of a solution of sodium methylate in methanol (0.001 equivalent). The resulting mixture is heated under a nitrogen atmosphere to a temperature of 155° C. There are then added, little by little over a period of 1.25 hours, 15 g of glycidol (0.195 epoxide equivalents). There is thus obtained a light colored wax dispersible in water.

EXAMPLE 14

Preparation of a mixture of compounds of formula (I) in which R is a tetradecyl radical and $n$ has the mean statistical value of 4.

After melting 26 g of hexadecane 1,2-diol (0.1 M) there is added under a nitrogen atmosphere 0.007 equivalent of sodium methylate. The resulting mixture is then heated to 150° C and 31 g of glycidol (0.4 epoxide equivalent) are added over a period of 1 hour 45 minutes. The product thus obtained is a light colored wax soluble in water and in 40% NaOH. Its Kraft point, measured at a 1% concentration, is 38° C. Its cloud point is above 95° C in both demineralized water and water containing 10% NaCl.

The foam heights measured by the Ross-Miles apparatus, at 35° C, for concentrations of 0.5%, 0.2% and 0.05% are, respectively, 15.5 cm, 13 cm and 7 cm.

EXAMPLE 15

Preparation of a mixture of compounds of formula (I) wherein R is an octadecyl radical and $n$ has the mean statistical value of 7.

31.5 g (0.1 mole) of eicosane 1,2-diol are heated up to melting under a light stream of nitrogen. There is then added 0.270 g of sodium methylate and the resulting mixture is heated to 155° C, at which point there are introduced, little by little, 56.5 g of glycidol (0.7 equivalent) over a period of 1 hour 30 minutes. There is thus obtained a light brown wax soluble in water and 40% NaOH, having a Kraft point of 47° C and a cloud point greater than 100° C in both demineralized water and in water containing 10% NaCl.

EXAMPLE 16

Preparation of a mixture of compounds of formula (I) wherein R is an octadecyl radical and $n$ has the mean statistical value of 10.

To 31.5 g of melted eicosane 1,2-diol (0.1 mole) there is added 0.27 g of sodium methylate (0.005 equivalent) under a nitrogen atmosphere. The mixture is heated to 155° C at which point there are added 81 g of glycidol (1 equivalent) over a period of 1 hour 45 minutes. After cooling there is thus obtained a light brown wax soluble in water and in 40% NaOH, having a Kraft point for a 1% solution of 55° C and a cloud point greater than 100° C in a 0.5% solution in water or in water containing 10% NaCl.

EXAMPLE 17

A very fine emulsion is prepared which has the following composition by weight %.

| | |
|---|---|
| Mixture of compounds prepared in Example 2 | 12% |
| Paraffin oil | 28% |
| Water | 60% |

The emulsion that is obtained is a cleaning lotion that is gentle in application.

EXAMPLE 18

An emulsion is prepared which has the following composition in % by weight:

| | |
|---|---|
| Mixture of compounds prepared in Example 2 | 6.3% |
| Glycerol monostearate | 2.7% |
| Perhydrosqualene | 15% |
| Purcellin oil | 6% |
| Water | 70% |

This emulsion is a makeup base.

EXAMPLE 19

Non-ionic shampoo

| | |
|---|---|
| Compounds obtained according to Example 1 | 15 g |
| Lauryl diethanolamide | 2 g |
| Carboxymethyl cellulose | 0.3 g |
| Water, q.s.p. | 100 g |
| pH of the solution is 7. | |

On application to the hair, a very abundant foam is rapidly attained.

The above example is repeated except that the mixture of compounds of Example 1 is replaced (a) by the mixture of compounds of Example 10 and (b) by the mixture of compounds of Example 11. In both instances, essentially similar effective shampoo compositions are produced.

EXAMPLE 20

Cationic shampoo

| | |
|---|---|
| Compounds prepared as in Example 1 | 7 g |
| Dimethyl hydroxyethyl cetyl ammonium bromide | 3 g |
| Hydroxypropyl methyl cellulose | 0.25 g |
| Lactic acid, q.s.p. | pH 3 |
| Water, q.s.p. | 100 g |

The presence of the compounds prepared as in Example 1 promotes formation of foam and allows easier rinsing of the hair. Besides, the hair is more readily untangled than when it is washed with a conventional cationic shampoo.

The above example is repeated except that the mixture of compounds of Example 1 is replaced (a) by the mixture of compounds of Example 10 and (b) by the mixture of compounds of Example 11. In both instances essentially similar effective shampoo compositions are produced.

EXAMPLE 21

Infant shampoo

| | |
|---|---|
| Compounds as in Example 1 | 5 g |
| R—NH—CH—COONa<br>　　　　　\|　　　　　　　　／C$_2$H$_5$<br>　　　　CH$_2$—CONH—(CH$_2$)$_3$—N<br>　　　　　　　　　　　　　　　　　　＼C$_2$H$_5$ | 3 g |
| (R: hydrocarbon radical of a coprah amine) | |
| Lauryl polyoxyethylene alcohol with 12 moles ethylene oxide per mole alcohol | 5 g |
| Lauryl diethanolamide | 1.5 g |
| Lactic acid, q.s.p. | pH 5 |
| Water, q.s.p. | 100 g |

The above example is repeated except that the mixture of compounds of Example 1 is replaced (a) by the mixture of compounds of Example 10 and (b) by the mixture of compounds of Example 11. In both instances, essentially similar effective shampoo compositions are produced.

EXAMPLE 22

Infant shampoo

| | |
|---|---|
| Compounds prepared as in Example 1 | 8 g |
| $\begin{array}{c}\text{OH}\\\text{\|}\quad\text{CH}_2\text{—COONa}\\\text{C}_{11}\text{H}_{23}\text{—C——N}\\\text{\|\|}\quad\text{\|}\quad\text{CH}_2\text{—CH}_2\text{—O—CH}_2\text{—COONa}\\\text{N}\quad\text{CH}_2\\\quad\diagdown\quad\diagup\\\quad\text{CH}_2\end{array}$ | 20 g |
| (sold under the tradename Miranol C2M) | |
| Lanolin polyoxyethylene alcohols with 75 moles ethylene oxide, sold as LANTROL AWS by Malstrom Chemical Corporation, Linden, N.J. | 0.3 g |
| Hydroxypropyl ethyl cellulose | 0.3 g |
| Lactic acid, q.s.p. | pH 8 |
| Water, q.s.p. | 100 g |

This composition and the one above are only slightly irritating to the eyes and have a good foaming action. They are suitable for baby shampoo.

The above example is repeated except that the mixture of compounds of Example 1 is replaced (a) by the mixture of compounds of Example 10 and (b) by the mixture of compounds of Example 11. In both instances essentially similar effective shampoo compositions are produced.

EXAMPLE 23

Anionic shampoo

| | |
|---|---|
| Compounds prepared as in Example 1 | 10 g |
| Condensation product of fatty acids of coprah on polypeptides sold as Maypon 4 CT by Maywood Division - Stepan Chemicals, N.J. | 30 g |
| Condensation product of undecylenic acid on protein hydrolysis products sold as Maypon UD by Maywood Division - Stepan Chemicals, N.J. | 5 g |
| Carboxymethyl cellulose | 0.4 g |
| Water, q.s.p. | 100 g |
| pH | 7 |

The above example is repeated except that the mixture of compounds of Example 1 is replaced (a) by the mixture of compounds of Example 10 and (b) by the mixture of compounds of Example 11. In both instances essentially similar effective shampoo compositions are produced.

EXAMPLE 24

Dye shampoo (foaming)

| | |
|---|---|
| Compound as in Example 1 | 10 g |
| Oxyethylenated nonylphenol with 4 moles ethylene oxide | 30 g |
| Diethanolamide of coprah | 15 g |
| Ethyl alcohol, 96° | 5 g |
| Propylene glycol | 15 g |
| Ammonia, 22° Be | 12 ml |
| Dyes: | |
| Meta diamino anisol sulfate | 0.030 g |
| Resorcinol | 0.400 g |
| Meta aminophenol base | 0.150 g |
| Para aminophenol base | 0.087 g |
| Nitro paraphenylene diamine | 0.004 g |
| Paratoluylenediamine | 1 g |
| Sodium salt of ethylene diamine tetraacetic acid | 3 g |
| Sodium bisulfite d = 1.32 | 1.200 ml |
| Water, q.s.p. | 100 g |

50 Grams of this composition are mixed in a basin with the same amount of hydrogen peroxide, 20 volumes, and the gel that is obtained is brushed onto the hair with a small brush. This is rubbed in until a foam is obtained. It is allowed to act for 30 minutes and the hair is then rinsed and dried.

On hair having a brown coloration there is obtained a chestnut hue.

EXAMPLE 25

Preparation of a mixture of compounds of formula (I) in which R is the radical R'—CHOH—CH$_2$—S—CH$_2$—, with R' being a mixture of alkyl groups, tridecyl to hexadecyl, and $n$ has a mean statistical value of 9.

The initial alpha diol is prepared by condensation of thioglycerol on a mixture of fatty chain oxiranes, sold under the name of NEDOX 1518 by the Archer Daniels Midland Co.

To 5.4 g of thioglycerol (0.05 equivalent) there are added 0.7 g of methanol solution of sodium methylate at 4.9 meq/g and then, drop by drop, at a temperature of 80°–85° C, 12.6 g (0.05 equivalent) of NEDOX 1518.

The reaction is exothermic during the whole addition, which requires 10 minutes.

A nitrogen atmosphere is used.

Fifteen minutes after the conclusion of the addition, there are no more free —SH groups. The product is heated to 150° C with elimination of the methanol from the sodium methylate solution and there are added, dropwise, in the course of 45 minutes, 33.3 g (0.45 equivalent) glycidol.

The product obtained is a brown wax, soluble in water and in 40% NaOH.

The Kraft point is 30°–32° C. The cloud point is above 100° C in demineralized water and in a 10% NaCl aqueous solution.

EXAMPLE 26

Lather bath

| Compound of formula (I) as in Example 3 | 7 g |
|---|---|
| Triethanolamine sulfate of dodecyl-tetradecyle | 12 g |
| Diethanolamide of coprah | 8 g |
| Cellulose ether | 3 g |
| Lactic acid q.s.p. | pH 7 |
| Water, q.s.p. | 100 g |

This composition is a slightly opalescent viscous liquid.

15 to 20 g of this composition diluted in a water bath i.e. 100–150 liters of water, produce a very important volume of lather. This lather is characterized by the fact that it is thick, consistent, stable, very pleasant to use and that it does not break down when soap is used, as the calcium and magnesium salts present in hard water are dispersed by the compound of formula (I).

EXAMPLE 27

An eye makeup remover lotion is prepared which has the following weight percent composition:

| Allantoin | 0.025% |
|---|---|
| Rose water | 20.000% |
| Mixture of compounds prepared in Example 10 | 0.500% |
| Methyl paraoxybenzoate (preservative) | 0.200% |
| Sterile demineralized water, q.s.p. | 100% |

The above components are mixed cold to provide a homogeneous formulation.

EXAMPLE 28

An eye makeup remover lotion is prepared which has the following weight percent composition:

| Allantoin | 0.025% |
|---|---|
| Rose water | 20.000% |
| Mixture of compounds prepared in Example 11 | 0.500% |
| Miranol C2M (as in Example 22) | 0.500% |
| Methyl paraoxybenzoate | 0.200% |
| Sterile demineralized water, q.s.p. | 100% |

The above components are mixed cold to provide a homogeneous formulation.

EXAMPLE 29

A makeup remover milk is prepared which has the following weight percent composition:

| Part A | |
|---|---|
| Vaseline oil | 10.000 |
| Isopropyl palmitate | 5.000 |
| Stearic acid | 1.400 |
| Glycerol stearate | 2.000 |
| Triethanolamine, pure | 0.700 |
| Part B | |
| Carboxyvinyl polymer, of high molecular weight, sold under the tradename Carbopol 941 by B. F. Goodrich Chemical Co. | 0.250 |
| Sterile demineralized water | 9.750 |
| Part C | |
| Pure triethanolamine | 0.250 |
| Part D | |
| Sterile demineralized water, q.s.p. | 100.00 |
| Methyl paraoxybenzoate | 0.200 |
| Part E | |
| Mixture of compounds prepared in Example 11 | 0.250 |
| Miranol C2M (as in Example 22) | 0.250 |
| Sterile demineralized water | 5.00 |
| Part F | |
| Perfume, sufficient to impart desired scent | |

In preparing the emulsion which constitutes the above makeup remover milk, Part A is heated to 85° C. Part D is heated to 95° C. Parts B and D are introduced into a preparation vessel and the resulting mixture is heated to 80° C at which point Part C is added thereto. After this addition, Part A is added to the mixture of Parts B, C and D with the aid of a turbo agitator. The resulting mixture of Parts A, B, C and D is then cooled and Parts E and F are added thereto at 30° C.

EXAMPLE 30

A makeup remover milk is prepared which has the following weight percent composition:

| Part A | |
|---|---|
| Vaseline oil | 10.000 |
| Isopropyl palmitate | 5.000 |
| Stearic acid | 1.400 |
| Glycerol stearate | 2.000 |
| Triethanolamine, pure | 0.700 |
| Part B | |
| Carboxyvinyl polymer of high molecular weight, sold under the tradename Carbopol 941 by B. F. Goodrich Chemical Co. | 9.750 |
| Part C | |
| Triethanolamine, pure | 0.250 |
| Part D | |
| Sterile demineralized water, q.s.p. | 100 % |
| Methyl paraoxy benzoate | 0.200 |
| Part E | |
| Mixture of compounds prepared in Example 11 | 0.500 |
| Sterile demineralized water | 5.000 |
| Part F | |
| Perfume, sufficient to impart desired scent | |

In preparing the emulsion which constitutes the above makeup remover milk, Part A is heated to 85° C. Part D is heated to 95° C. Parts B and D are introduced into a preparation vessel and the resulting mixture is heated to 80° C at which point Part C is added thereto. After this addition, Part A is added to the mixture of Parts B, C and D with the aid of an agitator. The resulting mixture of Parts A, B, C and D is then cooled and Parts E and F are added thereto at 30° C.

EXAMPLE 31

A makeup remover milk is prepared which has the following weight percent composition:

| | |
|---|---|
| Mixture of compounds prepared in accordance with Example 14 | 9.100 |
| Mixture of compounds prepared in accordance with Example 13 | 3.900 |
| Vaseline oil | 32.500 |
| Methyl paraoxybenzoate (preservative) | 0.200 |
| Demineralized water | 54.300 |

The mixtures of compounds prepared in accordance with Examples 13 and 14 are admixed at 80° C to provide a homogeneous mixture. The vaseline oil and preservative are then added at 80° C with agitation. Then the demineralized water is added at 80° C and the resulting mixture is emulsified with the aid of a turbo agitator for a period of 10 minutes. The resulting emulsion is then cooled to 25° C.

EXAMPLE 32

A cream hair straightener composition is prepared from the following components:

| | |
|---|---|
| Stearin | 3 g |
| Vaseline oil | 20 g |
| Vaseline (petroleum jelly) | 20 g |
| Olive oil | 10 g |
| Mixture of compounds prepared in accordance with Example 1 | 1 g |
| Coprah monoethanol amide | 5.5 g |
| Lithium hydroxide | 3.9 g |
| Water, q.s.p. | 100 g |

The above composition is applied to curled hair for 15 minutes, after which the hair is rinsed and then shampooed.

EXAMPLE 33

An aerosol shampoo composition is prepared from the following components:

| | |
|---|---|
| Part A | |
| Mixture of compounds prepared in accordance with Example 11 | 20 g |
| Coprah diethanolamide | 1.5 g |
| Dimethyl hydroxyethyl cetyl ammonium chloride | 1.5 g |
| Perfume | 0.2 g |
| Water, q.s.p. | 100 g |
| Part B | |
| 50:50 mixture of dichlorodifluoromethane and 1,2-dichloro-1,1,2,2-tetra fluoroethane | 10 g |

90 g of Part A are admixed with Part B and packaged under pressure in a conventional aerosol container to provide an aerosol shampoo formulation.

What is claimed is:

1. A mixture of compounds having the formula

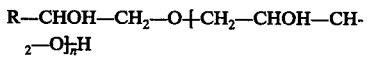

wherein R is a mixture of alkyl radicals having 9-2 carbon atoms and $n$ has a mean statistical average value of 3.5.

2. A mixture of compounds having the formula

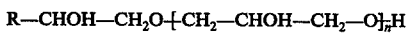

wherein R is dodecyl and $n$ has a mean statistical average value of 3.5.

3. A mixture of compounds having the formula

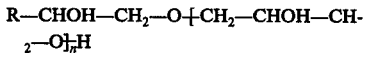

wherein R is a mixture of decyl and dodecyl and $n$ has a means statistical average value of 3.

4. The mixture of compounds of claim 3 wherein R is a 50:50 mixture by weight of decyl and dodecyl.

* * * * *